United States Patent [19]

Meador

[11] Patent Number: 4,861,333
[45] Date of Patent: Aug. 29, 1989

[54] ANIMAL ASPIRATING AND IRRIGATING APPARATUS

[76] Inventor: Lawrence D. Meador, P.O. Box 94, Lanark, Ill. 61046

[21] Appl. No.: 106,875

[22] Filed: Oct. 13, 1987

[51] Int. Cl.$^4$ ............................................. A61M 1/00
[52] U.S. Cl. ......................................... 604/35; 604/39
[58] Field of Search ................. 604/19, 35, 39, 73, 604/902

[56] References Cited

U.S. PATENT DOCUMENTS

| | | | |
|---|---|---|---|
| 750,276 | 1/1904 | Gruss | 604/39 |
| 1,828,986 | 10/1931 | Stevens | 604/39 |
| 2,148,541 | 2/1939 | Dierker | 604/35 |
| 2,860,636 | 11/1958 | Seitchik et al. | 604/35 |
| 4,294,251 | 10/1981 | Greenwald et al. | 604/35 |
| 4,681,564 | 7/1987 | Landreneau | 604/29 |
| 4,692,140 | 9/1987 | Olson | 604/35 |
| 4,715,848 | 12/1987 | Beroza | 604/35 |

Primary Examiner—C. Fred Rosenbaum
Assistant Examiner—Kathleen A. Daley
Attorney, Agent, or Firm—Leydig, Voit & Mayer, Ltd.

[57] ABSTRACT

Apparatus for aspirating and irrigating the rumen of a cow includes a nozzle connected to one end of a flexible tube and adapted to be slid down the cow's throat and inserted into the rumen. The other end of the tube is connected to a container which is adapted to be placed in a vacuumized condition by a hand-operated suction pump. When the pump is operated, toxic liquid and food in the cow's rumen is sucked into the nozzle, through the tube and into the container. A second tube is located in the first tube and is adapted to eject a spray of water for cleaning the nozzle and for irrigating the rumen. The water is contained in a tank which may be pressurized by compressed air at a veterinarian's office.

13 Claims, 2 Drawing Sheets

ANIMAL ASPIRATING AND IRRIGATING APPARATUS

BACKGROUND OF THE INVENTION

This invention relates generally to apparatus for aspirating and irrigating an organ of a non-human mammal such as a cow or a horse.

At times, the rumen (first stomach) of a cow becomes filled with toxic water and heavily compacted silage or grain which makes the cow ill. To relieve the problem, it is necessary to extract the toxic material from the rumen.

The apparatus of the invention also has applicability in connection with a mare which has just foaled. In such a case, it is desirable that the uterus of the mare be flushed and that placenta particles be removed therefrom.

SUMMARY OF THE INVENTION

The general aim of the present invention is to provide new and improved animal aspirating and irrigating apparatus which is very effective in use and which is easily portable for use by veterinarians at sites where no power or water is available.

A more detailed object of the invention is to provide portable apparatus having a nozzle which may be inserted into the organ and which may be used both to suck material from the organ and to irrigate the organ with water or other liquid.

Still another object of the invention is to provide novel apparatus which is operable to both aspirate and irrigate the organ by means of a single nozzle and without need of withdrawing the nozzle from the organ between the aspirating and irrigating operations.

The invention also resides in the provision of means for cleaning the nozzle in the event the nozzle becomes clogged and in the provision of a very simple and effective hand-operated pump operable to create suction for aspirating the organ.

These and other objects and advantages of the invention will become more apparent from the following detailed description when taken in conjunction with the accompanying drawings.

DETAILED DESCRIPTION OF THE PREFERRED EMBODIMENT

Figure 1:
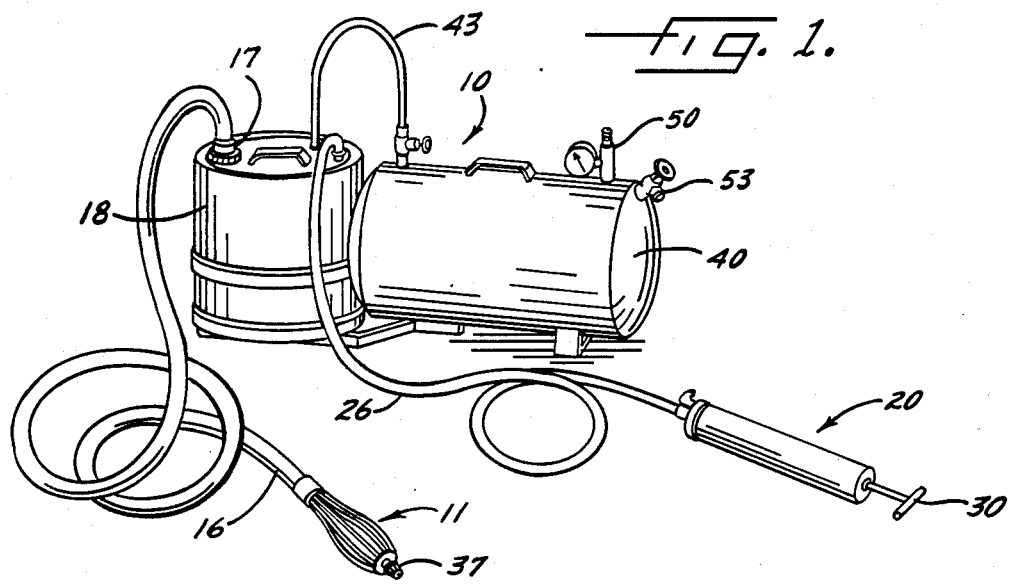
FIG. 1 is a perspective view of new and improved aspirating and irrigating apparatus incorporating the unique features of the present invention.

For purposes of illustration, the present invention has been shown in the drawings in conjunction with aspirating and irrigating apparatus 10 which is especially adapted for use by veterinarians in treating the organs of animals such as cows or horses. By way of example, the rumen of a cow may become filled with toxic liquid and compacted food which must be eliminated in order to prevent possible death of the cow.

The present invention contemplates the provision of new and improved aspirating apparatus 10 which may be used in an effective and simple manner. The apparatus is particularly characterized in that it may be transported to a farm by a veterinarian and used at a site where electrical and water service may not be available.

Figure 4:
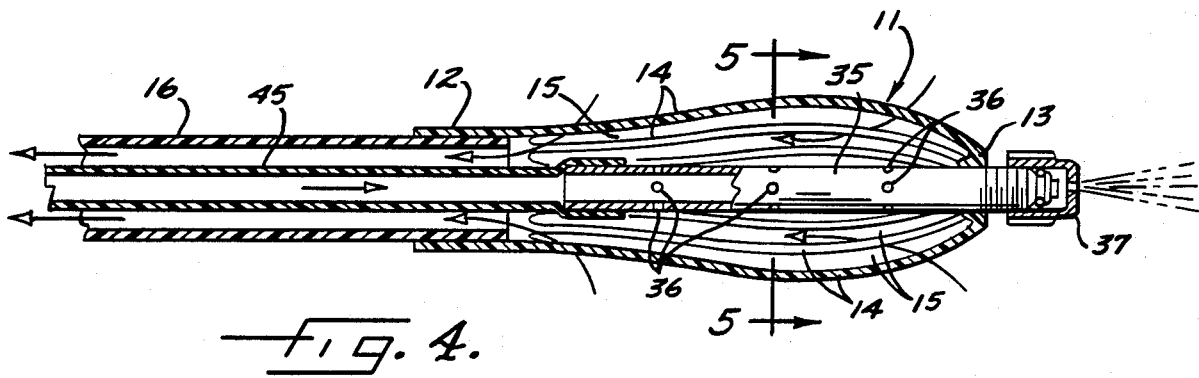
FIG. 4 is an enlarged fragmentary cross-section taken substantially along the line 4—4 of FIG. 2.

More specifically, the apparatus 10 includes a nozzle 11 which, in the case of a cow, is adapted to be slid down the throat of the cow and inserted into the cow's rumen. In this instance, the nozzle 11 is substantially bullet-shaped for ease of insertion and is made of relatively rigid plastic. As shown most clearly in FIGS. 2 and 4, the upstream end of the nozzle is defined by a sleeve 12 while the downstream end of the nozzle is defined by a nose 13. Formed integrally with and extending axially between the sleeve and the nose are several elongated strips or webs 14 which are spaced angularly from one another. Elongated ports 15 (FIG. 4) are defined by the spaces between the webs 14.

Connected to the sleeve 12 of the nozzle 11 and communicating with the ports 15 thereof is an elongated flexible tube 16. A fitting 17 on the opposite end portion of the tube 16 connects the tube with a plastic container 18 which serves to hold material extracted from the cow's rumen.

Figure 2:
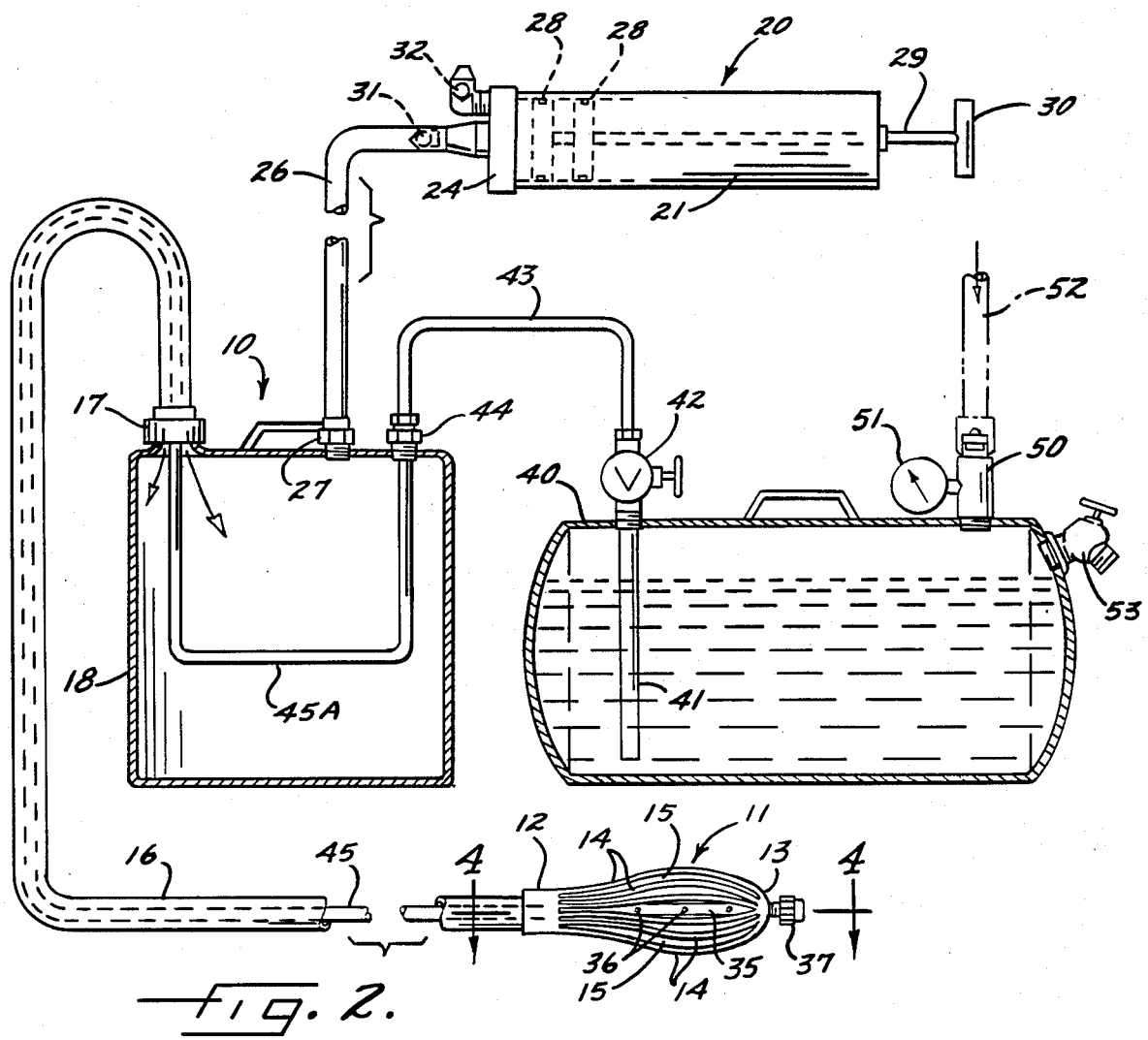
FIG. 2 is a view partly in elevation and partly in section and schematically illustrating the apparatus of FIG. 1.
Figure 3:
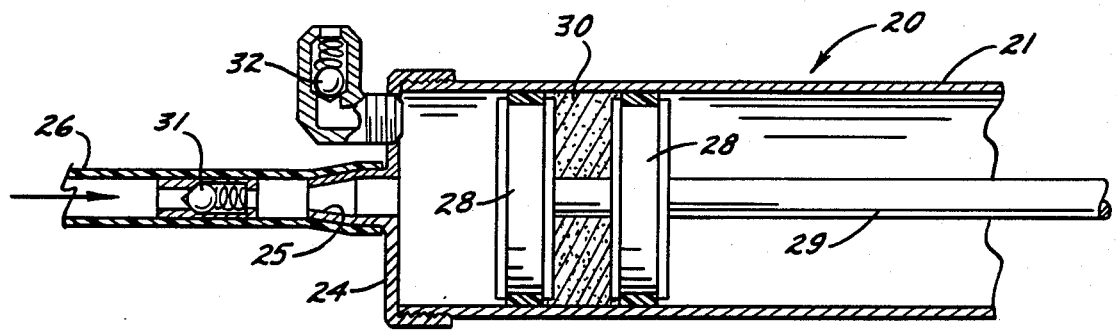
FIG. 3 is an enlarged fragmentary cross-sectional view of the suction pump of the apparatus.
Figure 5:
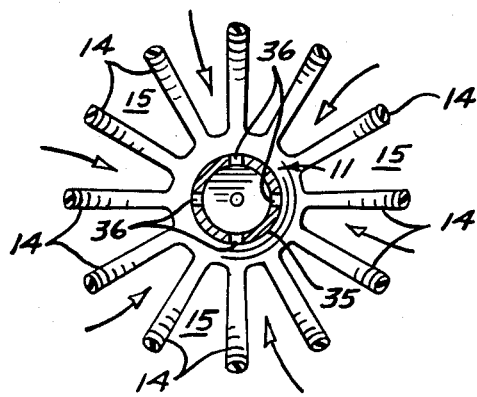
FIG. 5 is an enlarged cross-section taken along the line 5—5 of FIG. 4 and shows the nozzle in its aspirating mode.

The material is extracted by using a hand-operated pump 20 to create a negative pressure in the container 18 and the tube 16 and thereby cause liquid and solids in the rumen to be sucked into the ports 15 of the nozzle 11 (see FIG. 5) for flow through the tube and then into the container. Herein, the pump 20 includes a cylinder 21 (FIG. 3) having an end cap 24 with a sleeve 25 which is telescoped tightly into one end of a flexible tube 26 whose other end is connected to the container 18 by a fitting 27 (FIG. 2). Telescoped into the cylinder are two axially spaced pistons 28 (FIG. 3) which are connected to a rod 29 having a handle 30 for use in reciprocating the pistons back and forth in the cylinder. Advantageously, a quantity 30 of viscous, semi-solid material such as jelled grease, petroleum jelly or heavy wax is packed into the space between the two pistons. The semi-solid material establishes an excellent seal between the pistons and the inner wall of the cylinder to enable the pump 20 to draw a vacuum in an efficient manner.

When the pistons 28 of the pump 20 are retracted from left to right (FIG. 3), a negative pressure is created in the cylinder 20 and the tube 26. A check valve 31 (FIG. 3) in the tube 26 opens to enable a vacuum to be drawn in the container 18, the tube 16 and the nozzle 11 so as to cause material to be sucked from the cow's rumen and into the container. During retraction of the pistons, a check valve 32 which is connected to the cap 24 is in a closed position to enable a vacuum to be drawn in the cylinder. When the pistons are advanced from right to left, the check valve 32 opens to enable air in the cylinder to exhaust to atmosphere and, at the same time, the check valve 31 closes in order to hold the vacuum in the tube 26 and the container 18.

Figure 6:
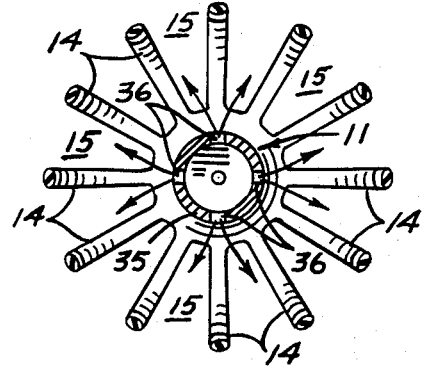
FIG. 6 is a view similar to FIG. 5 but shows the nozzle in its irrigating mode.

As material is sucked into the nozzle 11, it is likely that the ports 15 between the webs 14 eventually will become clogged with solids. Pursuant to the invention, provision is made for unclogging the nozzle and also for irrigating the rumen with water so as to flush the rumen and help loosen compacted food therein. For this purpose, an elongated conduit or pipe 35 (FIG. 4) made of copper or the like is located within the nozzle 11 and is adapted to be supplied with pressurized water for cleaning the ports 15 and irrigating the rumen. Three axially spaced rows of angularly spaced holes 36 are formed in the pipe and are adapted to spray jets of water toward the ports 15 in order to force solid material out of the ports (see FIG. 6). In addition, the end portion of the pipe 35 extends through the nose 13 of the nozzle 11 and supports a spray nozzle 37 which shoots water directly into the rumen. The nozzle 37 is connected threadably to the end portion of the pipe 35 and may be selectively adjusted to change the pattern of the spray or to shut the spray down altogether.

Novel means are provided for directing pressurized water into the pipe 35 without need of having an external pressure source located at the site. Herein, these means comprise a second container or tank 30 (FIGS. 1 and 2) adapted to be filled with water or other suitable irrigating liquid. A vertical pipe 41 is connected to a shut off valve 42 and extends nearly to the bottom of the tank. Connected to the valve 42 is a line 43 which, by way of a fitting 44 on the container 18, is connected to a flexible tube or hose 45 having one end portion 45A located in the container. The other end portion of the hose 45 extends out of the container 18 through the fitting 17, extends through the tube 16 and is connected to the upstream end of the pipe 35.

In keeping with the invention, a valved fitting in the form of a quick-connect air valve 50 (FIG. 2) with a pressure gage 51 is attached to the tank 40. When a line 52 leading from a compressed air supply (not shown) is coupled to the valve 50, the tank 40 may be pressurized in order to provide a motive force for causing water to flow from the tank.

With the foregoing arrangement, the veterinarian may pressurize the tank 40 at his office with a compressed air supply, the valve 42 being closed during pressurization of the tank. After the apparatus 10 has been transported to the farm, the veterinarian inserts the nozzle 11 and the tubes 16 and 45 down the cow's throat and into the rumen. The hand pump 20 then is operated to suck toxic fluid from the rumen and into the container 18.

If the ports 15 in the nozzle 11 become clogged, the plastic container 18 tends to collapse inwardly when the pump 20 is operated. Upon detecting this, the veterinarian may open the valve 42. As a result, the pressurized air in the tank 40 forces the water in the tank through the pipe 43 and the hose 45. The water is ejected from the holes 36 in the pipe 35 and cleans the clogged material from the ports 15. Even if the ports do not clog, the veterinarian may wish to irrigate the rumen with water to loosen compacted food and make it easier to suck the food from the rumen. Thus, upon opening of the valve 43, water is sprayed into the rumen by way of the holes 36 as well as through the nozzle 37 and serves to flush the rumen prior to the next pumping cycle.

As shown in FIG. 2, another valved fitting 53 is connected to the tank 40 and is adapted to be connected to a conventional garden hose. If a water supply is available at the site, the veterinarian may wish simply to couple a garden hose to the fitting 53 and use the water pressure to force water from the tank 40.

From the foregoing, it will be apparent that the present invention brings to the art new and improved aspirating and irrigating apparatus 10 which is easily transportable and which may be used at locations where water and power facilities are not available. In addition to being useful in sucking toxic material from the cow's rumen, the apparatus may be used for other purposes as, for example, to clean and irrigate the uterus of a mare or other large animal after the animal has given birth.

I claim:

1. Apparatus for aspirating and irrigating an organ of a non-human mammal, said apparatus comprising a nozzle shaped for insertion into the organ and having a plurality of ports, a first flexible tube having one end portion communicating with said nozzle, a first portable container for holding an opposite end portion communicating with said container, a suction pump communicating with said container and selectively operable to create a negative pressure in said container, said tube and said nozzle thereby to suck material from said organ into said ports and said nozzle, through said tube, and into said container, a second flexible tube located within said first tube and having one end portion communicating with said nozzle, a second portable container adapted to hold a liquid for irrigating said organ, said second tube having an opposite end portion communicating with said second container, means within said first container for establishing communication between said second container and said opposite end of said second tube, and means on said second container for admitting pressure fluid into said second container for the purpose of pressuring said second container in order to force said liquid out of said second container, through said second tube and said nozzle, and out of said ports so as to remove clogged material from said ports and to irrigate said organ.

2. Apparatus as defined in claim 1 in which said nozzle is elongated and is formed with a plurality of angularly spaced webs, said ports being defined by the spaces between said webs.

3. Apparatus as defined in claim 1 further including tubular means located within said nozzle and communicating with said second tube, and at least one row of angularly spaced holes formed in said tubular means and defining passages permitting said liquid to flow into said nozzle.

4. Apparatus as defined in claim 3 in which axially spaced rows of angularly spaced holes are formed through said tubular means.

5. Apparatus as defined in claim 3 further including a second nozzle on one end of said tubular means and operable to cause said liquid to spray axially out of said tubular means.

6. Apparatus as defined in claim 5 in which said tubular means extends axially through said first nozzle, said second nozzle being located on the downstream end of said tubular means and being positioned outside of said first nozzle.

7. Apparatus as defined in claim 6 in which said second nozzle is selectively adjustable in order to change the spray emitted from said second nozzle.

8. Apparatus as defined in claim 1 in which said means on said second container comprise a valved fitting for admitting pressurized air into said second container.

9. Apparatus as defined in claim 1 in which said means on said second container comprise a valved fitting for admitting pressurized liquid into said second container.

10. Apparatus as defined in claim 1 in which said means on said second container comprise first and second valved fittings for respectively admitting pressurized air and pressurized liquid into said second container.

11. Apparatus as defined in claim 1 in which said suction pump comprises a cylinder, a pair of pistons spaced axially from one another within said cylinder and adapted to be reciprocated in unison in the cylinder, and a viscous semi-solid material packed between said pistons and operable to establish a seal between said pistons and said cylinder during reciprocation of said pistons.

12. Apparatus for aspirating and irrigating an organ of a non-human mammal, said apparatus comprising a nozzle shaped for insertion into the organ and having a plurality of ports, a first flexible tube having one end portion communicating with said nozzle, a first container for holding material aspirated from said organ, said tube having an opposite end portion communicating with said container, a hand-operated suction pump communicating with said container and selectively operable to create a negative pressure in said tube and said nozzle thereby to suck material from said organ into said ports and said nozzle, through said tube, and into said container, a second flexible tube located within said first tube and having one end portion communicating with said nozzle, a second container adapted to hold a liquid for irrigating said organ, means located within said first container for establishing communication between said second container and the opposite end of said second tube, and a valved fitting communicating with said second container for admitting compressed air into and retaining compressed air in said second container for the purpose of pressurizing said second container in order to force said liquid out of said second container, through said second tube and said nozzle, and out of said ports so as to remove clogged material from said ports and to irrigate said organ.

13. Apparatus as defined in claim 12 further including a second valved fitting on said second container and adapted to communicate with a garden hose for admitting pressurized water into said second container.

* * * * *